United States Patent
Madsen (10) Patent No.: US 12,011,530 B2
(45) Date of Patent: Jun. 18, 2024

(54) SYSTEMS AND METHODS FOR COLLECTION OF INCREASED VOLUMES OF IgG DURING PLASMA COLLECTION PROCEDURES

(71) Applicant: Fenwal, Inc., Lake Zurich, IL (US)

(72) Inventor: James Madsen, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 280 days.

(21) Appl. No.: 17/352,928

(22) Filed: Jun. 21, 2021

(65) Prior Publication Data

US 2022/0023522 A1 Jan. 27, 2022

Related U.S. Application Data (60) Provisional application No. 63/055,391, filed on Jul. 23, 2020, provisional application No. 63/055,403, filed on Jul. 23, 2020.

(51) Int. Cl.
*A61M 1/34* (2006.01)

(52) U.S. Cl.
CPC ................. *A61M 1/3496* (2013.01)

(58) Field of Classification Search
CPC ....... A61M 1/34; A61M 1/303; A61M 1/3496
See application file for complete search history.

(56) References Cited

U.S. PATENT DOCUMENTS

| | | | |
|---|---|---|---|
| 5,171,456 A * | 12/1992 | Hwang | A61M 1/3672 210/257.2 |
| 5,188,588 A * | 2/1993 | Schoendorfer | A61M 1/302 604/6.07 |
| 5,194,145 A | 3/1993 | Schoendorfer | |
| 5,360,542 A | 11/1994 | Williamson, IV et al. | |
| 5,401,262 A * | 3/1995 | Karwoski | A61M 1/602 604/321 |
| 5,722,964 A * | 3/1998 | Herweck | A61M 1/742 604/317 |
| 6,210,383 B1 * | 4/2001 | Want | A61M 1/61 604/318 |

OTHER PUBLICATIONS

Burkhardt et al., Immunoglobulin G levels during collection of large volume plasma for fractionation; Transfusion 2017; 56:417-420.
Extended European Search Report for European Application No. 21186548.0 dated Dec. 10, 2021.

* cited by examiner

*Primary Examiner* — Ariana Zimbouski
(74) *Attorney, Agent, or Firm* — Cook Alex Ltd.

(57) ABSTRACT

A plasmapheresis system and a method for operating a plasmapheresis system are provided by which the reservoir for the concentrated red blood cells (RCC) has a first chamber for receiving anticoagulant used for priming the separator and purging the system of air prior to the initial draw cycle and a second chamber for receiving separated red blood cells. Because the entire volume of second chamber of the RCC reservoir may now receive separated red blood cells and no AC prime volume, a greater amount of whole blood may be processed in the first draw cycle, thus resulting in a greater total volume of Immunoglobulin G (IgG) being collected during the plasmapheresis procedure.

6 Claims, 10 Drawing Sheets

SYSTEMS AND METHODS FOR COLLECTION OF INCREASED VOLUMES OF IgG DURING PLASMA COLLECTION PROCEDURES

BACKGROUND

The present application relates to systems and methods for performing plasmapheresis and, more particularly, to plasmapheresis systems and methods in which the volume of Immunoglobulin G collected during the procedure is increased.

Plasmapheresis is an apheresis procedure in which whole blood is withdrawn from a donor, the plasma separated from the cellular blood components (red blood cells, platelets and leukocytes) and retained, and the cellular blood components returned to the donor. The separation of the plasma from the cellular components is typically accomplished in an automated procedure by centrifugation or membrane filtration.

Plasma-derived therapies are provided through large plasma fractionation facilities at which many plasma donations are pooled together and then fractionated into its therapeutic components. Globally, the need for plasma-derived therapies in general, and Immunoglobulin G (IgG) in particular, is growing. IgG has multiple indications when used as intravenous or subcutaneous IgG, such as primary immunodeficiency, chronic inflammatory demyelinating polyneuropathy, multifocal motor neuropathy, secondary immunodeficiency, and others.

In automated plasmapheresis procedures, the plasma product is often collected in multiple collection and reinfusion cycles, until a total target volume of anticoagulated plasma has been collected. Recent literature suggests that donor blood IgG concentrations decrease throughout plasma collection procedures and exhibit the largest reduction after the first 200 mL of collected plasma. Specifically, a 9% drop of the donor's IgG occurs from the baseline of zero plasma collected (at the start of the procedure) to 200 mL of plasma collected, and a drop of an additional 4% from 200 mL to 800 mL collected. See, e.g., Burkhardt et al., Immunoglobulin G levels during collection of large volume plasma for fractionation; Transfusion 2017; 56:417-420. This was attributable to a shift of interstitial fluid equal to approximately 9% of the donor's initial total blood volume (after 200 mL of plasma being collected) to approximately 13% of the donor's initial total blood volume (after 800 mL of plasma being collected).

Because the source plasma from multiple donors is combined, it is important to maximize the IgG volume that may be collected from each individual donor, as even small gains in volume collected from each individual donor, when added together, result in a meaningful increase in the total volume of IgG in the pooled plasma. If systems and methods were developed that were able to maximize the volume of IgG collected during the first draw cycle of a plasmapheresis procedure, more IgG could be collected from each donor, increasing the overall volume of IgG produced at each plasma collection center. Accordingly, by way of the present disclosure, systems and methods are provided for optimizing the volume of IgG during a plasmapheresis procedure.

SUMMARY

By way of the present disclosure, systems and methods for operating a plasmapheresis system are provided that result in an increased the volume of IgG collected by increasing the volume of whole blood processed in the first collection cycle.

In a first aspect, a method is provided for performing a plasmapheresis procedure having a priming phase, at least one collection phase, and at least one reinfusion phase so as to maximize a volume of whole blood processed during a first draw phase. The method comprises a) providing a disposable fluid flow set having a plurality of tubing segments in fluid communication with a reservoir comprising a first chamber into which priming fluid is flowed during the priming phase and a second chamber into which a cell fraction comprising separated blood cells is flowed during the collection phase and from which the separated blood cells are flowed during the reinfusion phase; b) introducing a priming fluid into the disposable fluid flow set; c) flowing spent priming fluid into the first chamber of the reservoir; and d) occluding one or more of the tubing segments to prevent flow into or out from the first chamber.

In a second aspect, the method further comprises: a) introducing whole blood into the disposable fluid flow set; b) separating the whole blood into a plasma fraction and the cell fraction; and c) flowing the cell fraction into the second chamber of the reservoir.

In a third aspect, the method of further comprises flowing the cell fraction out of the second chamber.

In a fourth aspect, the method further comprises retaining the spent priming fluid in the first chamber of the reservoir and disposing it together with the disposable fluid flow circuit upon completion of the plasmapheresis procedure.

In a fifth aspect, the priming solution is an anticoagulant solution.

In a sixth aspect, a disposable fluid flow set for an apheresis system is provided comprising a separator; a first tubing segment connected to an outlet of the separator; a second tubing segment; and a reservoir comprising first and second internal chambers, each having a first port in fluid communication with the first tubing segment and a second port in fluid communication with the second tubing segment.

In a seventh aspect, the disposable fluid flow set further comprises a third tubing segment connecting the first port of the first internal chamber to the first tubing segment, a fourth tubing segment connecting the second port of the first internal chamber to the second tubing segment, a fifth tubing segment connecting the first port of the second internal chamber to the first tubing segment, and a sixth tubing segment connecting the second port of the second internal chamber to the second tubing segment.

In an eighth aspect, the first internal chamber has an open upper end permitting fluid from the first internal chamber to spill over into the second internal chamber.

In a ninth aspect, a system for performing a plasmapheresis procedure is provided that comprises a durable hardware component and the disposable fluid flow set of any of the sixth-eighth aspects above in which the durable hardware component comprises a first dual tube clamp for controlling flow through the third and fifth tubing segments, a second dual tube clamp for controlling flow through the fourth and sixth tubing segments, and a programmable controller programmed to automatically actuate the first and second dual tube clamps to selectively permit or preclude flow through the third, fourth, fifth and sixth tubing segments in connection with performing a priming, collection or reinfusion phase of a plasmapheresis procedure.

In a tenth aspect, a fluid container is provided comprising first and second internal chambers, each having a first port and a second port wherein the first internal chamber has an open upper end permitting fluid from the first internal chamber to spill over into the second internal chamber.

DETAILED DESCRIPTION

A more detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

By way of the present disclosure, systems and methods are provided for operating a plasmapheresis system to increase the volume of IgG collected in a plasmapheresis procedure by increasing the volume of whole blood processed in the first collection cycle. The amount of extracorporeal blood that can be processed in a single draw cycle is limited by the volume of the reservoir for receipt of the separated red blood cells ("red cell concentrate" or RCC). Because of the volume of anticoagulant (AC) that is used for priming and flushing the air out of the disposable set before introducing blood into the set is received in the RCC reservoir, the volume of extracorporeal blood that that can be processed in the first draw cycle is reduced by that volume of AC.

By way of the present disclosure, the amount of extracorporeal blood that can be processed in the first draw cycle is increased by providing the RCC reservoir with separate chambers for receipt of the AC prime volume and the separated red blood cells. The contents of the RCC chamber is returned to the donor after the completion of each collection phase, while the AC prime volume is maintained in the AC chamber throughout the procedure and is then thrown out with the disposable kit after the procedure is completed and the donor disconnected.

As further described herein, each of the AC chamber and RCC chamber has two ports with tubing segments associated therewith. A first pair of tubing segments comprising one tubing segment from each of the AC chamber and the RCC chamber is connected to the cell line of the disposable set, while a second pair of tubing segments comprising one tubing from each of the AC chamber and the RCC chamber is connected to the reinfusion line of the disposable set.

The hardware component of the system is provided with two dual tube clamps, one for each pair of tubing segments, that act on the tubing segments in each pair to alternately permit flow through one of the pair while preventing flow through the other of the pair, or to prevent flow through both tubing segments of the pair. During AC priming, the two dual tube clamps direct flow to the AC chamber within the RCC reservoir, and then, during plasma collection, the clamps direct flow of the separated red blood cells to the RCC chamber of the RCC reservoir. This allows for processing of the full extracorporeal blood volume in the first collection cycle, when donor IgG concentration is highest, resulting in additional IgG being collected for the procedure.

Turning now to the accompanying drawings, plasmapheresis is performed on an automated system comprising a hardware component, generally designated 10 (best seen in FIG. 1), and a disposable set, generally designated 12 (best seen in FIGS. 3-6, in which the disposable set is shown mounted to the hardware component), to collect plasma to be processed as source plasma. With reference to FIGS. 1-6, and as described in greater detail below, the disposable set 12 consists of an integrally connected separator, containers, and tubing to transport blood and solutions within a sterile fluid pathway.

Figure 2:
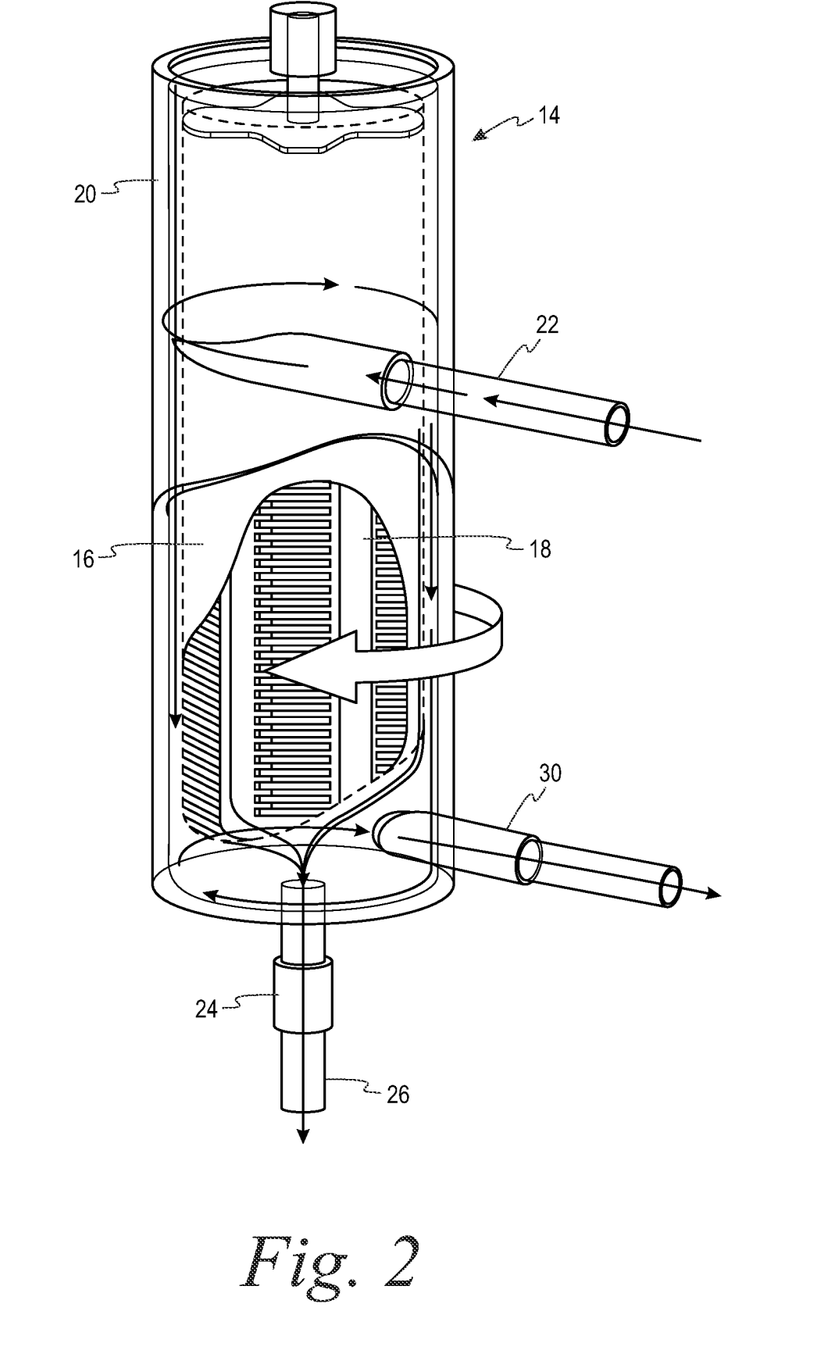
FIG. 2 is a perspective view of a spinning membrane separator of the type incorporated in a disposable set, with portions broken away to show detail, usable with the plasmapheresis system of FIG. 2.
Figure 3:
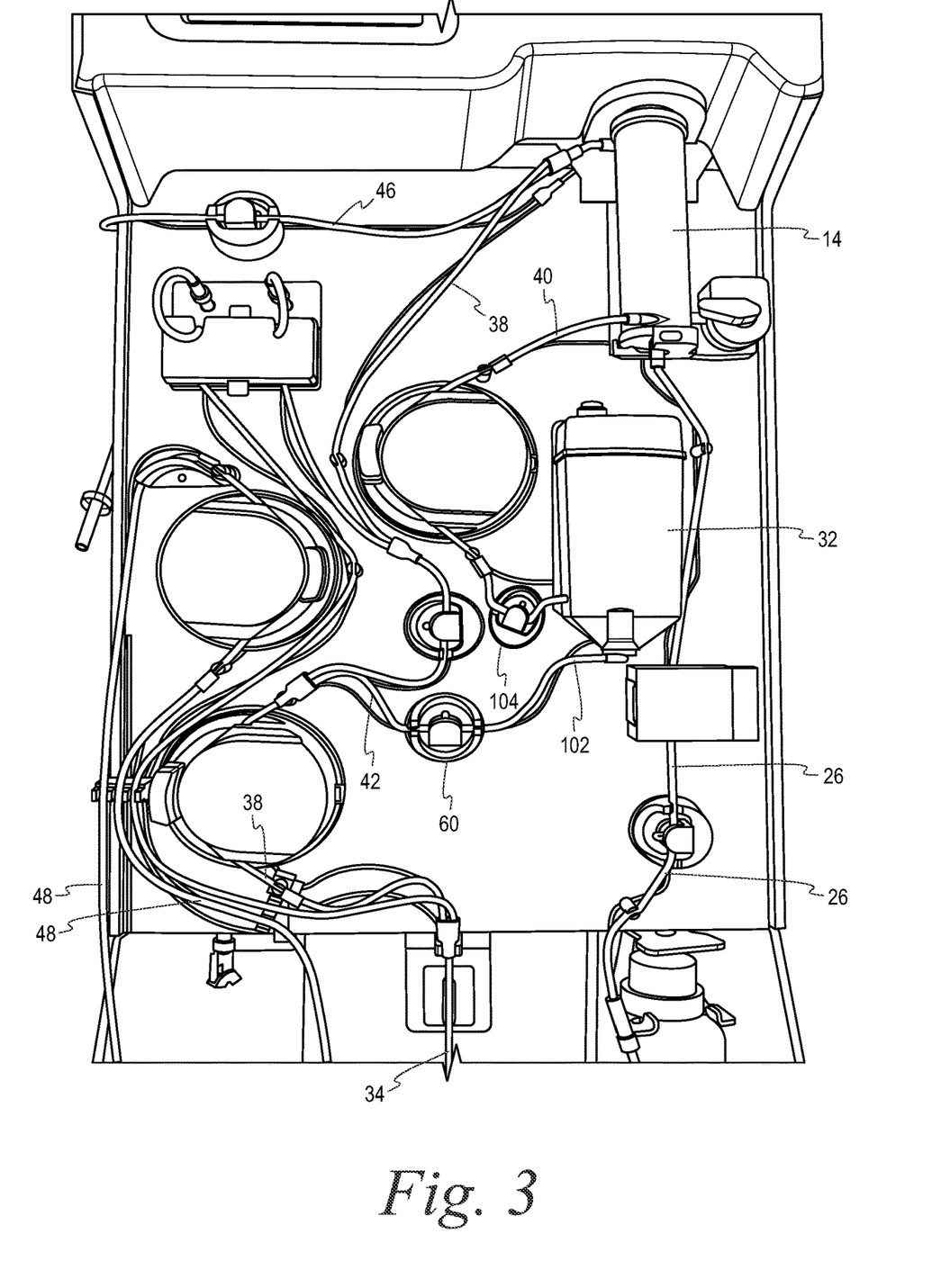
FIG. 3 is a perspective view of the front panel of the plasmapheresis system of FIG. 2 showing the components of the disposable set that are mounted thereto.

The separator 14, best seen in FIG. 2, has a spinning membrane filter 16 mounted to a rotor 18 for rotation within a case 20 to separate blood into components. A detailed description of a spinning membrane separator may be found in U.S. Pat. No. 5,194,145 to Schoendorfer, which is incorporated herein by reference. As can be appreciated, in a different system, separation of the whole blood may be accomplished by centrifugation. See, e.g. U.S. Pat. No. 5,360,542 to Williamson et al.

During plasmapheresis, anticoagulated whole blood enters the separator 14 through a whole blood input port 22. The plasma is separated by the spinning membrane filter and then passes out of a plasma output port 24, through a plasma line 26, and into a plasma collection container 28. Concentrated cells are pumped out of a concentrated cell output port 30 into a RCC reservoir 32 (described in greater detail below), where the cells remain until reinfusion to the donor.

The disposable set 12 also includes tubing lines for introducing whole blood from the donor into the system during collection and returning concentrated cells to the donor during reinfusion (donor line 34, which terminates in the venipuncture needle 36), and for transporting anticoagulated whole blood to the separator (blood line 38), concentrated cells into the reservoir (cell line 40), concentrated cells from the reservoir to the donor line (reinfusion line 42), plasma into the plasma collection container (plasma line 44), saline (saline line 46), and anticoagulant (AC line 48).

The hardware component 10 includes a programmable controller 50 and touch screen 52 with a graphical user interface ("GUI") through which the operator controls the procedure. For example, the GUI permits entry of any of a donor ID, donor sex, donor height, donor weight, donor age, donor hematocrit/hemoglobin; a target saline infusion volume (if a saline protocol is selected), and a target plasma volume. The touch screen 52 also enables the operator to gather status information and handle error conditions.

Three peristaltic pumps are located on the front panel of the hardware component 10, including an AC pump 54, a blood pump 56, and a cell pump 58. The AC pump 54 delivers anticoagulant solution (AC) at a controlled rate into the blood line 38 as whole blood enters the set from the donor. The blood pump 56 delivers anticoagulated whole blood to the separator during the collection phase of the procedure and returns concentrated cellular components and, if desired, replacement fluid to the donor during the reinfusion phase of the procedure. The cell pump 58 delivers concentrated cellular components from the separator 14 to a reservoir during the collection phase.

The front panel also includes four clamps into which various of the tubes of the disposable set 12 are installed, including a reinfusion clamp 60, a blood clamp 62, a saline clamp 64, and a plasma clamp 66. The reinfusion clamp 60 closes to block the reinfusion line (42) during the collection phase (FIG. 5) and is open during the reinfusion phase (FIG. 6) to allow the blood pump 56 to reinfuse the concentrated cellular components from the reservoir 32 to the donor. The blood clamp 62 opens during the collection phase to allow anticoagulated whole blood to be pumped to the separator 14 and closes during the reinfusion phase to block the blood line 38. The saline clamp 64 closes to block the saline line 46 during the collection phase and during reinfusion of the separated cellular components. If saline is to be used as a replacement fluid, the saline clamp 64 opens during the reinfusion phase. The plasma clamp 66 opens during the collection phase to allow plasma to flow into the plasma collection container 28 and closes during the reinfusion phase. As described in greater detail below, the reinfusion clamp 60 is a dual tube clamp, and a second dual tube clamp 104 is associated with the cell line 40 that leads to the inlet of the RCC reservoir 32.

Figure 1:
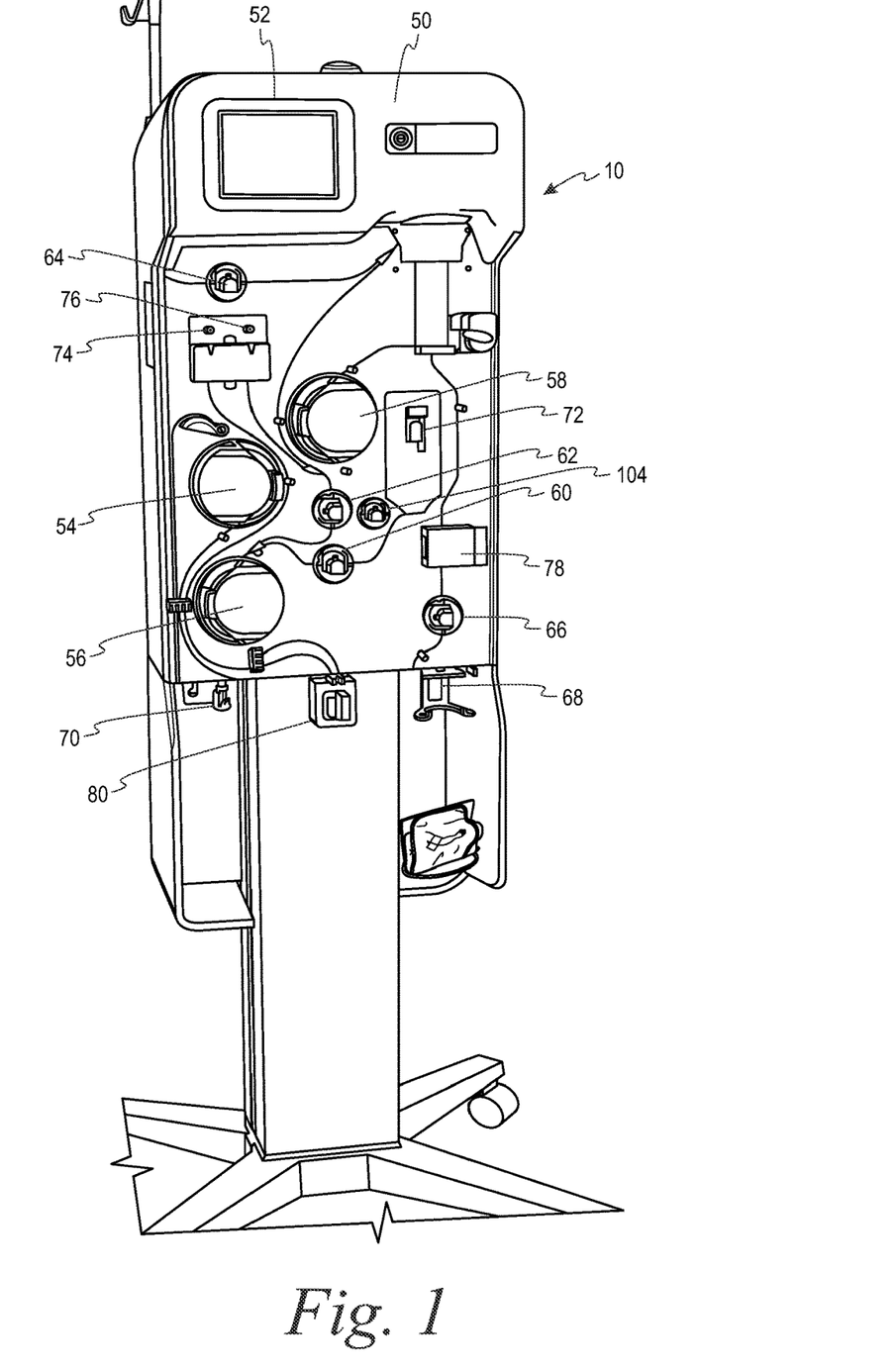
FIG. 1 is a perspective view of an exemplary plasmapheresis instrument suitable for use in the system and method of the present application.

With reference to FIG. 1, the hardware component 10 includes three weigh scales to monitor the current plasma collection volume (scale 68), the AC solution volume (scale 70), and the concentrated cellular content volume (scale 72). The system also includes various sensors and detectors, including a venous pressure sensor 74, a separator pressure sensor 76, optical blood detectors 78, and an air detector 80.

In keeping with the disclosure, the RCC reservoir 32 is provided with a separate AC chamber 82, for receipt of the AC prime volume, and a separate RCC chamber 84, for receipt of separated red blood cells. The size and volume of the RCC reservoir is restricted by regulations on the allowable extracorporeal volume of fluid drawn from a donor. Consequently, a separate AC chamber allows for the RCC chamber to be of the maximum permissible size and volume permits a volume of blood to be separated in the first draw cycle that results in the entire volume of the RCC chamber being filled with separated red blood cells.

The AC chamber 82 is open at its top end 86, such that additional AC prime volume due to alarms or error may spill over the top of the AC chamber 82 and into the RCC chamber 84. The AC chamber 82 includes two ports 88, 90 at its lower end, each having a tubing segment associated therewith. Tubing segment 92 is associated with port 88 and is in fluid communication with the cell line 40, while tubing segment 94 is associated with port 90 and is fluid communication with the reinfusion line 42. Similarly, the RCC chamber includes two ports 96, 98 at its lower end, each having a tubing segment associated therewith. Tubing segment 100 is associated with port 96 and is in fluid communication with the cell line 40, while tubing segment 102 is associated with port 98 and is fluid communication with the reinfusion line 42. Thus, tubing segments 92 and 100 form a first pair tubing segments that are connected (by, e.g., a Y-connector) to the cell line 40 and tubing segments 94 and 102 form a second pair of tubing segments that are connected (also by, e.g., a Y-connector) to the reinfusion line 42.

The hardware component of the system is provided with two dual tube clamps, one for each pair of tubing segments, that act on the tubing segments in each pair to alternately permit flow through one of the pair while preventing flow through the other of the pair, or to prevent flow through both tubing segments of the pair. Specifically, reinfusion clamp 60, described above, is a dual tube clamp that acts on tubing segments 94 and 102 to control flow through the reinfusion line 42. A second dual tube clamp 104 is provided that acts on tubing segments 92 and 100 to control flow through the cell line 40. During AC priming, the two dual tube clamps direct flow to the AC chamber within the RCC reservoir, and then, during plasma collection, the clamps direct flow of the separated red blood cells to the RCC chamber of the RCC reservoir. As can be appreciated, the controller can be preprogrammed to automatically actuate the dual tube clamps to control flow through its associated tubing segments for performance of the priming, collection and return phases of the plasmapheresis procedure, as described below.

The donor is connected to the system throughout the procedure. As illustrated, the disposable set 12 includes a single venipuncture needle 36, through which whole blood is drawn from the donor in a collection phase (FIG. 5) and concentrated cells are returned to the donor in a reinfusion stage (FIG. 6). As noted above, the plasmapheresis procedure may comprise a plurality of cycles each having a collection/separation phase followed by a return or reinfusion phase.

Prior to the first collection phase, the disposable set is primed with AC and air flushed from the set. During the collection phase, the whole blood is separated into plasma and concentrated cells, with the separated plasma being directed to a plasma collection container 28 and the separated red blood cells being directed to a reservoir 32. During the reinfusion phase, the concentrated red blood cells from the reservoir 32 are reinfused to the donor through the venipuncture needle 36.

Figure 4:
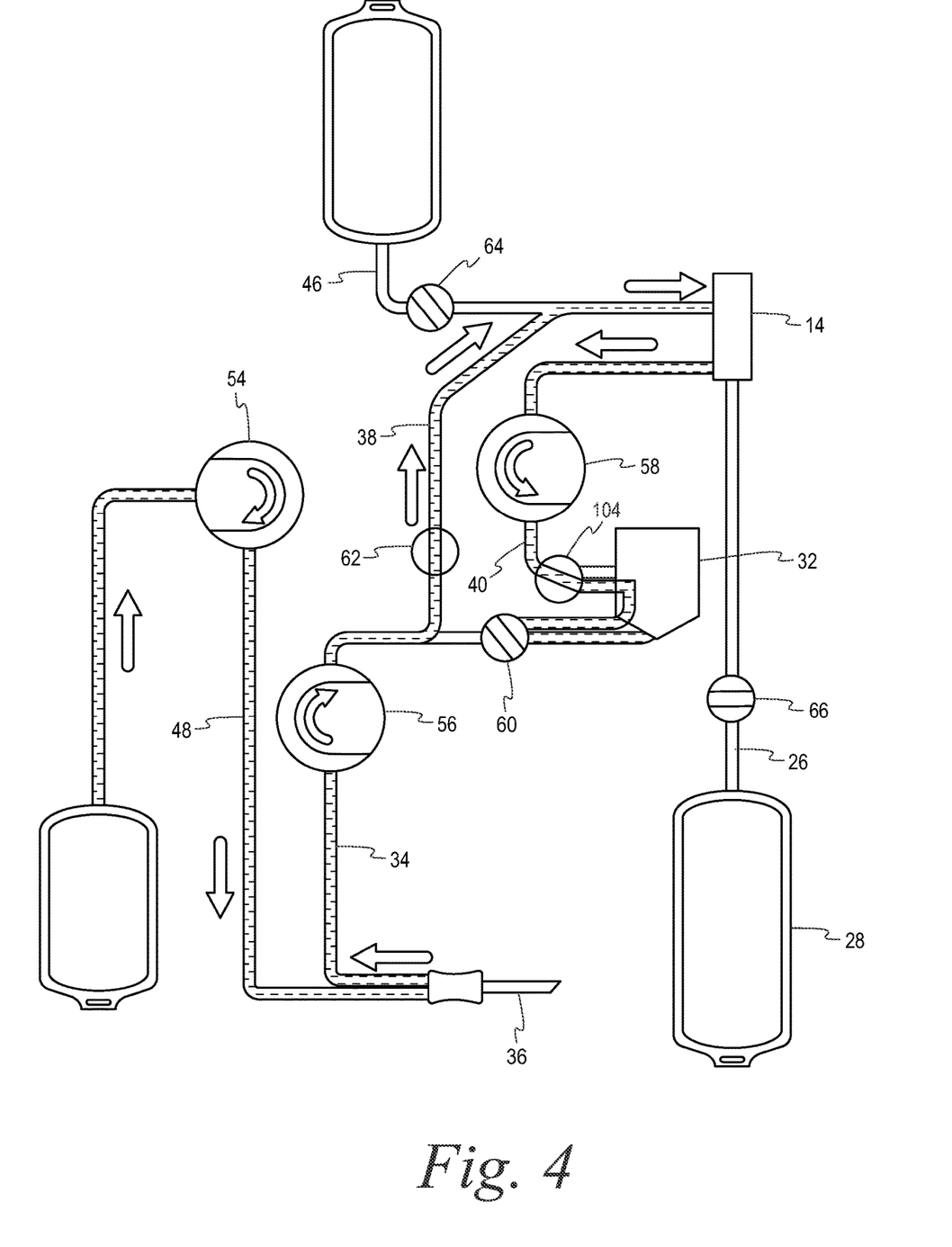
FIG. 4 is a schematic view showing operation of the plasmapheresis system in the priming phase.
Figure 7:
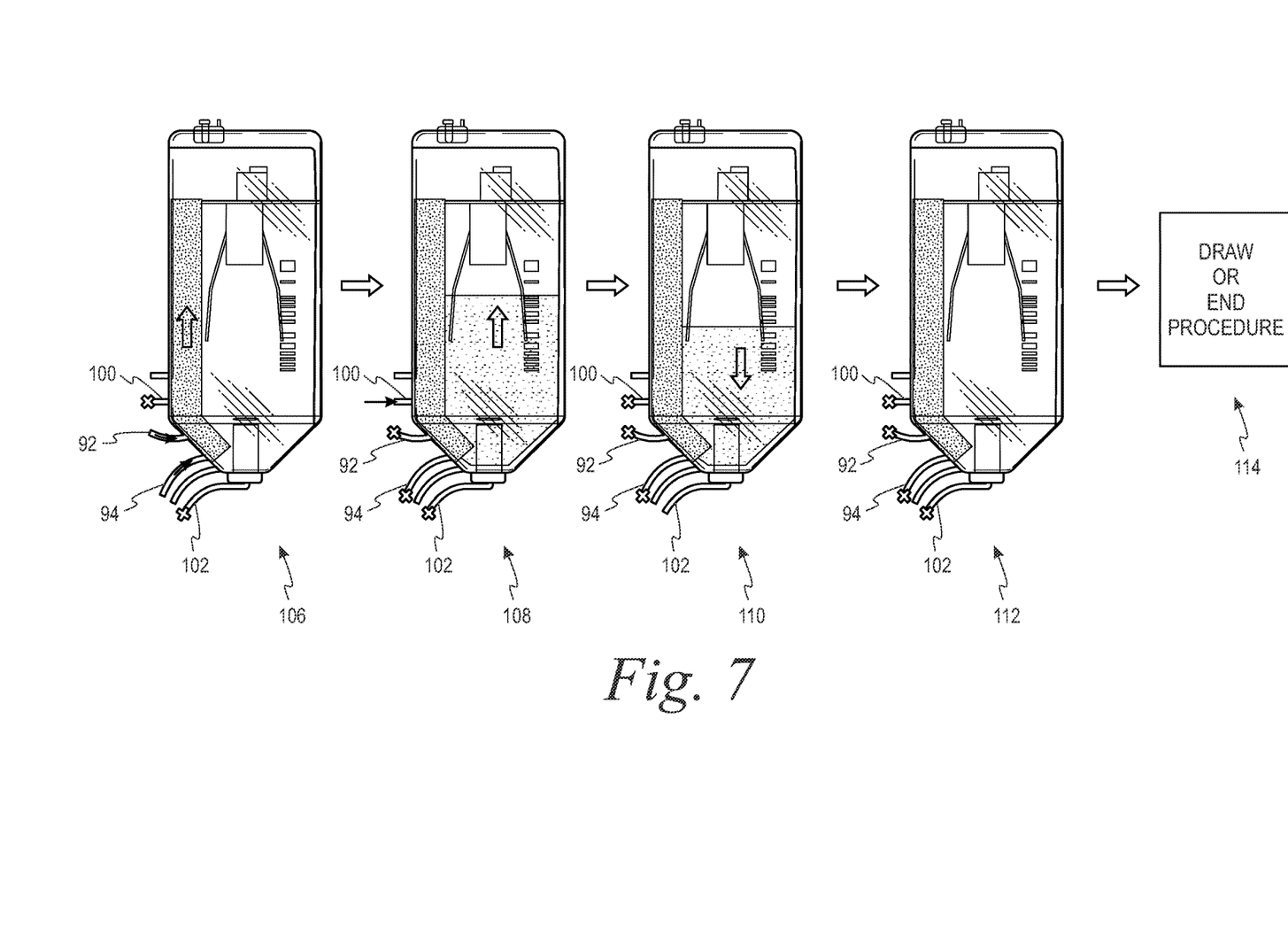
FIG. 7 sequentially illustrates the flow to the RCC collection container in accordance with the present disclosure during AC prime, during the first draw phase, during the first RCC return/reinfusion phase, and after the first RCC return/reinfusion phase, followed by either starting a subsequent draw phase or ending the procedure.
Figure 8A:
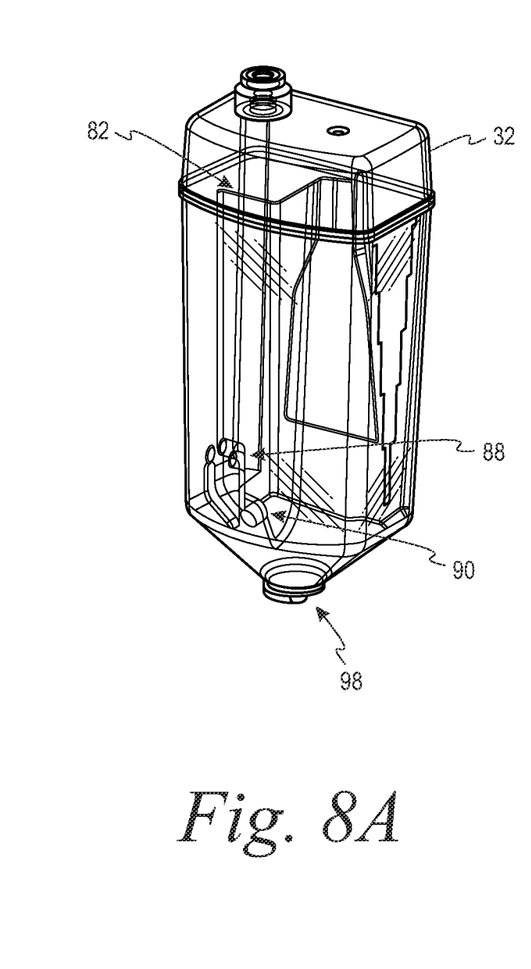
FIGS. 8a-8c are perspective, side and front views of an RCC collection container according to the present disclosure.
Figure 8B:
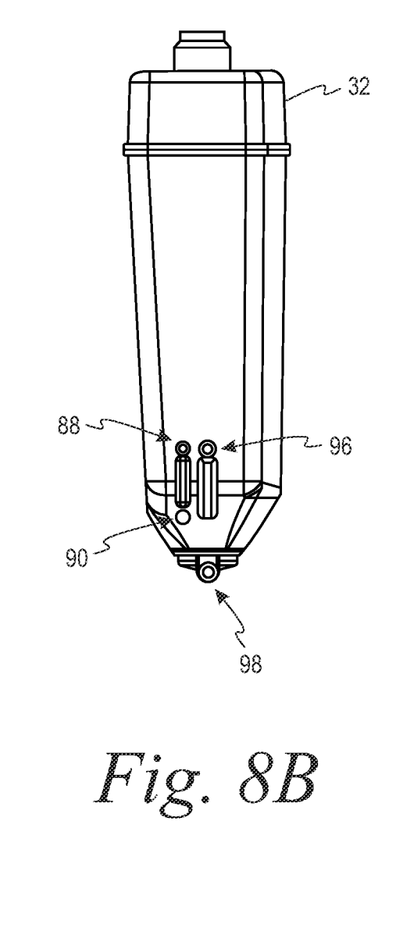
Figure 8C:
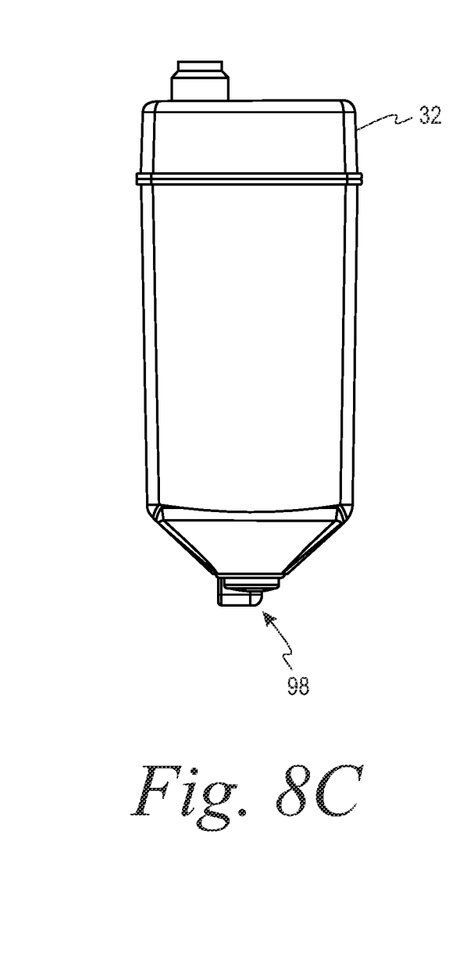
Figure 9A:
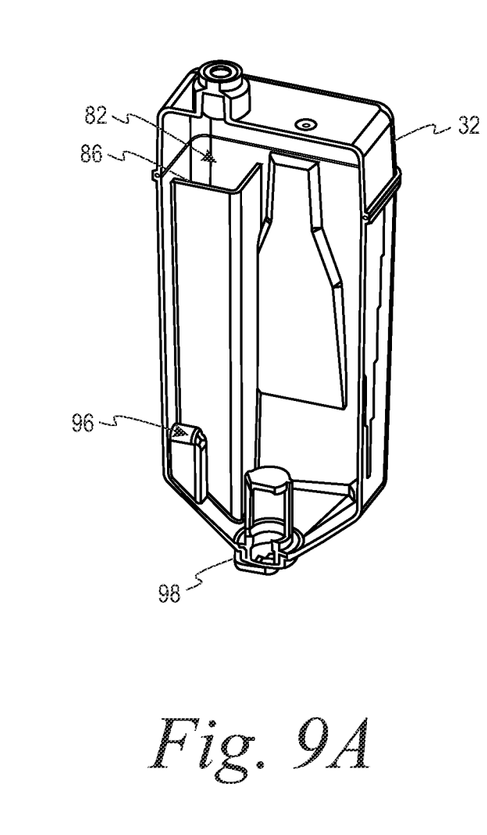
FIGS. 9a-9c are sectional views showing details as to the interior of the RCC collection container, with FIG. 9a being a perspective view with a vertical section being taken behind the front wall of the RCC collection container, FIG. 9b being a perspective view with a vertical section being taken behind the front wall of the AC chamber, and FIG. 9c being top view.
Figure 9B:
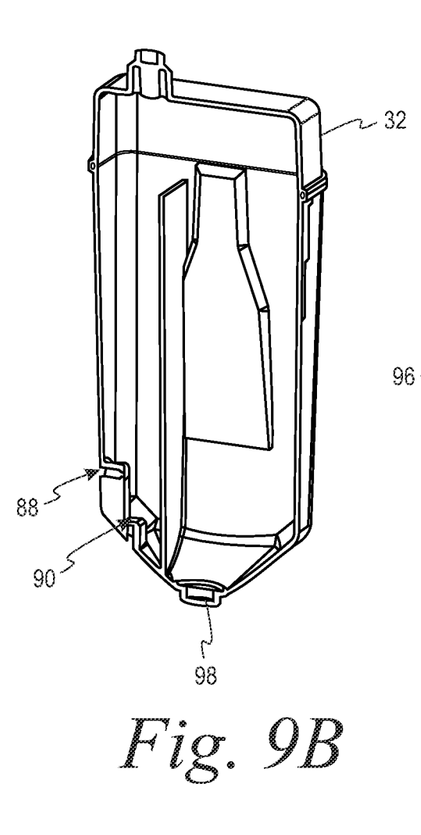
Figure 9C:
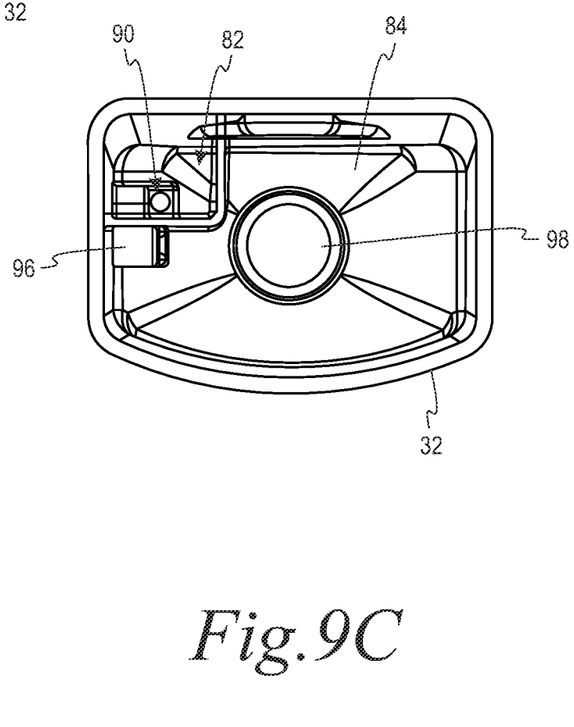
Figure 10:
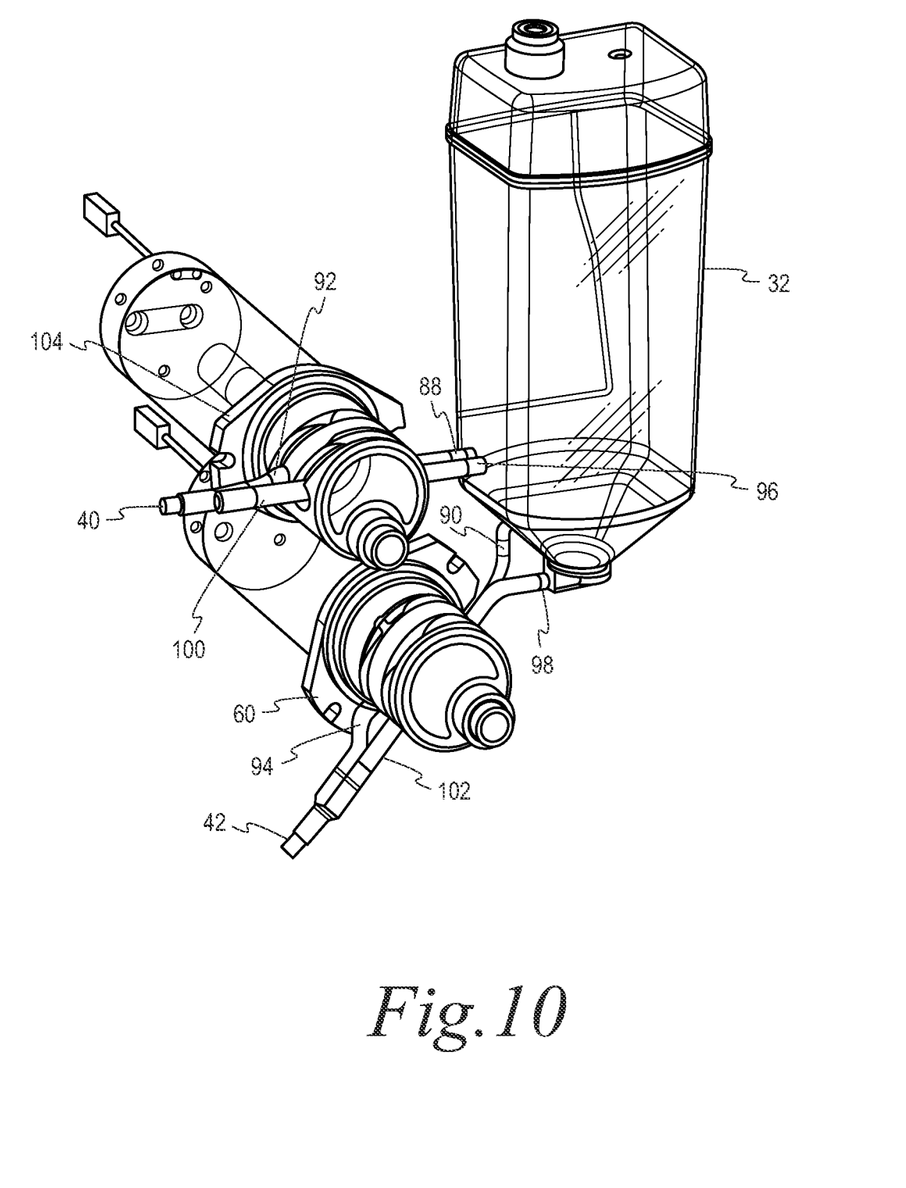
FIG. 10 is perspective view of the combination of the RCC collection container with associated tubing segments leading to the AC and RCC chambers and with dual tube clamps being associated with the tubing segments.

With reference to FIGS. 4 and 7, during the priming phase, anticoagulant solution (AC) is pumped at a controlled rate through the disposable set to prime the separator 14 and purge air from the disposable set. Dual tube clamp 104 is actuated to permit flow through tubing segment 92 into the AC chamber 82, but to block flow through tubing segment 100 into the RCC chamber 84. Dual tube clamp 104 is actuated to permit flow through tubing segment 94 into the AC chamber 82, but to block flow through tubing segment 102 into the RCC chamber. This permits the initial AC prime volume to fill the AC chamber 82 (FIG. 7 at 106). FIG. 4 shows dual tube clamp 60 blocking flow through both tubing segment 94 to the AC chamber and tubing segment 102 to the RCC chamber during the first state of the priming phase, while FIG. 7, at 106, shows flow into the AC chamber through both tubing segments 92 and 94 during the final state of the priming phase, such that both lines to the reservoir 32 have been flushed with AC to clear the air from the fluid pathways.

Figure 5:
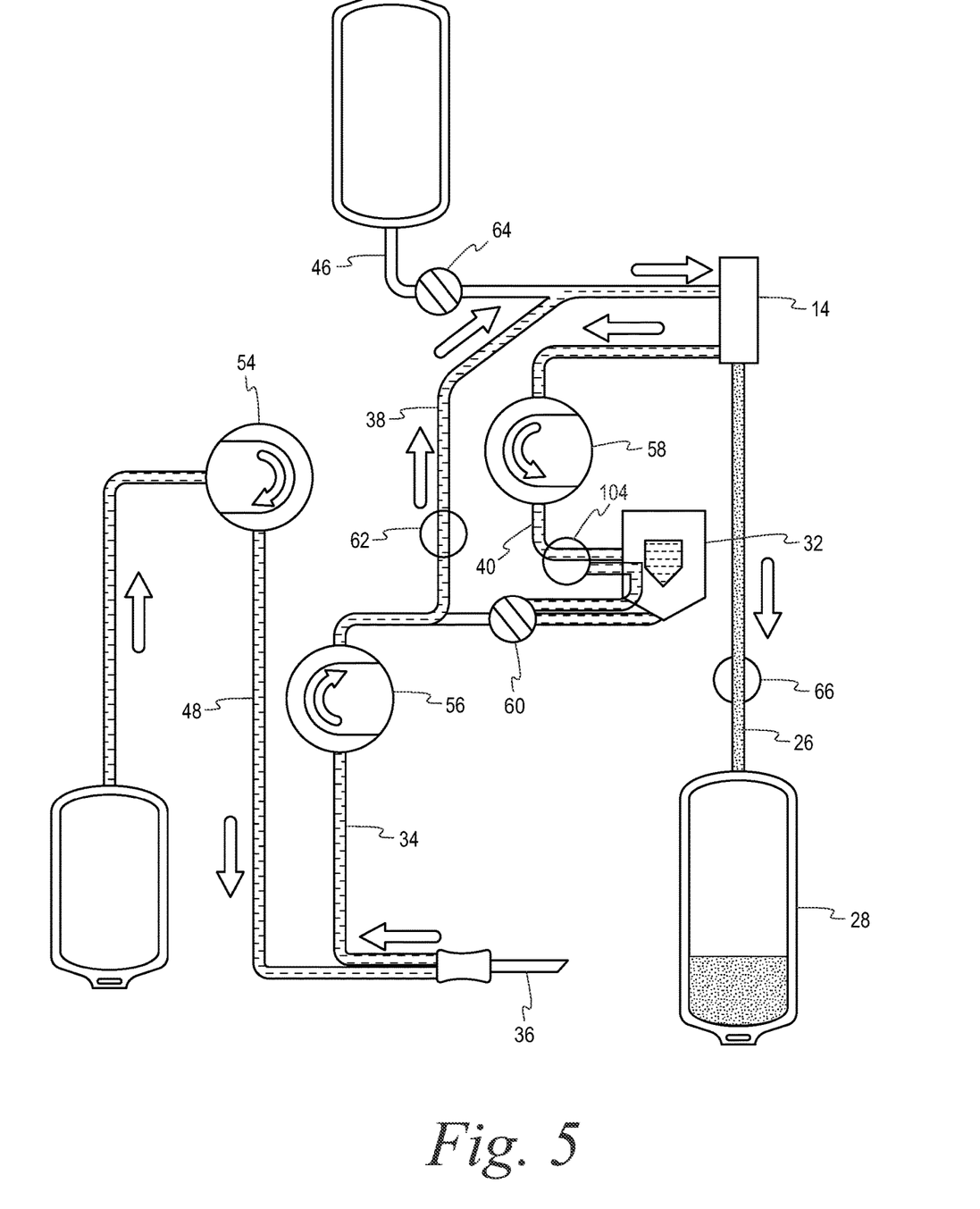
FIG. 5 is a schematic view showing operation of the plasmapheresis system in the collection phase.
Figure 6:
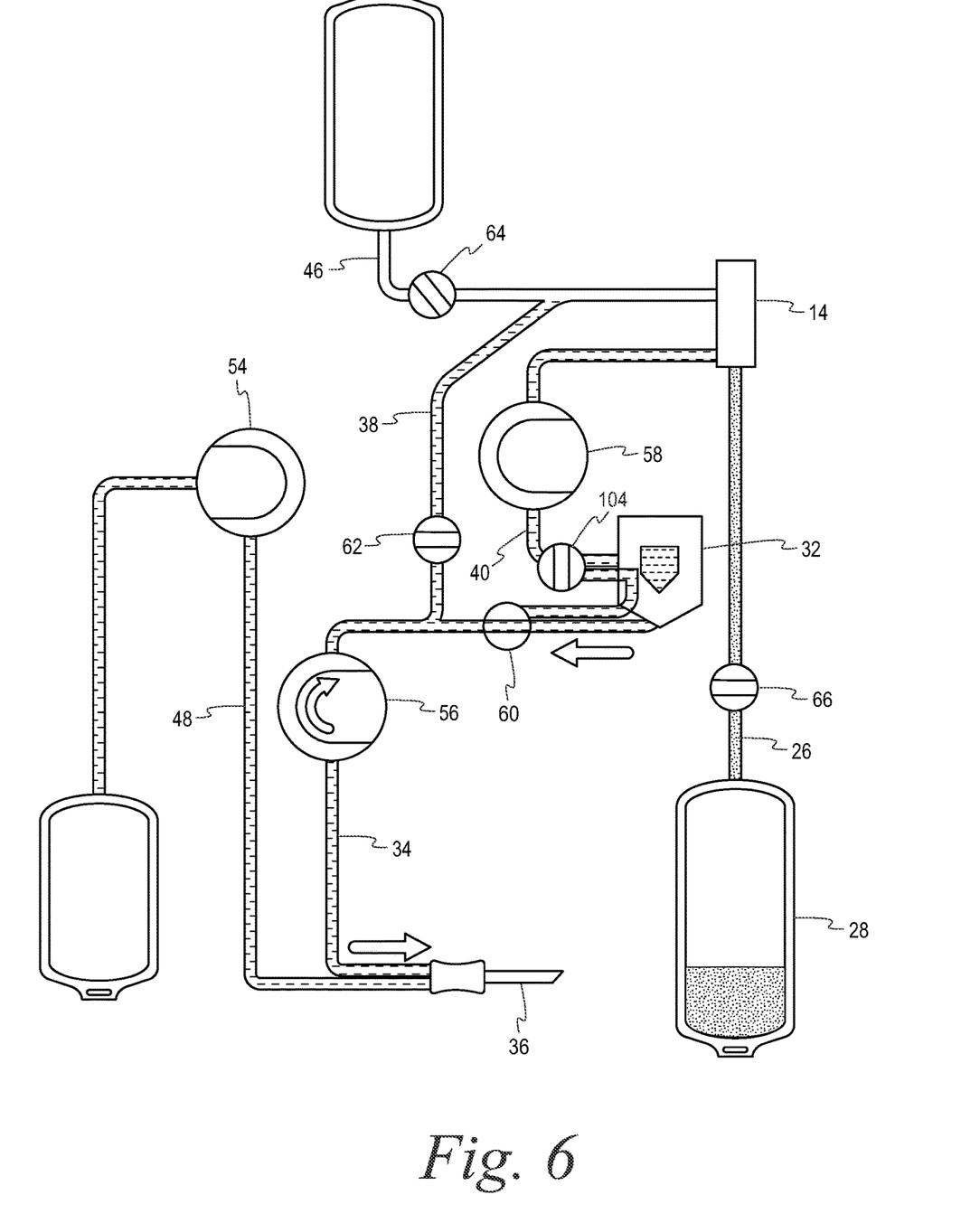
FIG. 6 is a schematic view showing operation of the plasmapheresis system in the return or reinfusion phase.

With reference to FIGS. 5 and 7, during the collection phase, AC is pumped at a controlled rate and mixed with whole blood as it enters the disposable set 12. The anticoagulated blood is pumped to the separator 14, where plasma is separated from the cellular components and directed to the plasma collection container 28. Dual tube clamp 104 is actuated to permit flow through tubing segment 100 into the RCC chamber, but to block flow through tubing segment 92 into the AC chamber, while dual tube clamp 60 is actuated to preclude flow through both tubing segment 94 from the AC chamber 82 and tubing segment 102 from the RCC chamber 84. Separated red blood cells are thus pumped from the separator 14 to the RCC chamber 84 of the reservoir 32 (FIG. 7 at 108). The collection phase stops when the reservoir 32 reaches an expected volume of separated red blood cells.

With reference to FIGS. 6 and 7, during the reinfusion phase, the blood pump 56 reverses direction and pumps the concentrated cells from the RCC chamber 84 of reservoir 32 back to the donor through the reinfusion line 34 and to the apheresis needle 36. Dual tube clamp 104 is actuated to prevent flow through both tubing segment 92 leading to the AC reservoir and tubing segment 100 leading to the RCC chamber, while dual tube clamp 60 is actuated to permit flow out of the RCC chamber 84 through tubing segment 102 and prevent flow out of the AC chamber 82 through tubing segment 94 (FIG. 7 at 110). After return of the RCC to the donor, dual tube clamp 60 is actuated to occlude both tubing segments 94 and 102 (FIG. 7 at 112). The system then proceeds to a subsequent draw cycle or ends the procedure (FIG. 7 at 114). As can be appreciated, the AC prime volume is maintained in the AC chamber 82 throughout the procedure and is not returned to the donor. If a saline protocol was selected, by which saline is returned to the donor as a replacement fluid for the collected plasma, the final reinfusion phase is followed by saline infusion.

The benefits of the system and methods described above in achieving an increase in the volume of IgG collected may be seen in the following examples.

Example 1. In the system of this example, the AC Prime volume is approximately 30 mL. The RCC collection container is provided with a separate AC chamber having a volume of approximately 30 mL, while the RCC chamber has a volume of 250 mL, so that a full volume of 250 mL of blood may be processed in the first collection cycle, rather than 220 mL if the AC Prime volume of 30 mL and separated red blood cells were combined together in the RCC collection container. With the additional 30 mL of separated red blood cells processed in the first collection cycle at 75% collection efficiency, for a donor hematocrit of 40, 54 mL of additional blood processed will contain 32.4 mL of additional plasma being processed (54 mL*0.6=32.4 mL). The 42.4 mL of additional plasma being processed at a 75% collection efficiency will yield 24.3 mL of extra plasma collected in the first collection cycle (42.4 mL*0.75=24.3 mL). The RCC collection container will receive an additional 29.7 mL of RCC (54 mL−24.3 mL), of which 8.1 mL is plasma (32.4 mL−24.3 mL), so that the hematocrit of the additional RCC of 29.7 mL is 73%. The 24.3 mL of extra plasma collected in this first cycle contains an increased concentration of 67 mg/dL IgG (Burkhardt et al. 2017) as compared to the second collection cycle, leading to an increased collection of 16.3 mg IgG per collection (24.3 mL*67 mg/dL).

Example 2. In the system of this example, the AC Prime volume is approximately 10 mL The RCC collection container is provided with a separate AC chamber having a volume of approximately 10 mL, while the RCC chamber has a volume of 200 mL, so that a full volume of 200 mL of blood may be processed in the first collection cycle, rather than 190 mL if the AC Prime volume of 10 mL and separated red blood cells were combined together in the RCC collection container. With the additional 10 mL of separated red blood cells processed in the first collection cycle at 75% collection efficiency, for a donor hematocrit of 40, 18 mL of additional blood processed will contain 10.8 mL of additional plasma being processed (18 mL*0.6=10.8 mL). The 10.8 mL of additional plasma being processed at a 75% collection efficiency will yield 8.1 mL of extra plasma collected in the first collection cycle (10.8 m*0.75=8.1 mL). The RCC collection container will receive an additional 9.9 mL of RCC (18 mL−8.1 mL), of which 2.7 mL is plasma (10.8 mL−8.1 mL), so that the hematocrit of the additional RCC of 9.9 mL is 73%. The 8.1 mL of extra plasma collected in this first cycle contains an increased concentration of 67 mg/dL IgG (Burkhardt et al. 2017) as compared to the second collection cycle, leading to an increased collection of 5.4 mg IgG per collection (8.1 mL*67 mg/dL).

The methods and system set forth above have several aspects. In a first aspect, a method for collecting plasma in which plasma product is collected in multiple collection phases between which separated red blood cells are reinfused to the donor is provided.

It will be understood that the embodiments described are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope of the claims is not limited to the above-description, but is set forth in the following claims.

The invention claimed is:

1. A disposable fluid flow set for an apheresis system comprising:
   e) a separator;
   f) a first tubing segment connected to an outlet of the separator;
   g) a second tubing segment; and
   h) a reservoir comprising first and second internal chambers, each of said first and second chambers having a first port in fluid communication with the first tubing segment and a second port in fluid communication with the second tubing segment wherein the first internal chamber has an open upper end permitting fluid from the first internal chamber to spill over into the second internal chamber.

2. The disposable fluid flow set of claim 1 further comprising a third tubing segment connecting the first port of the first internal chamber to the first tubing segment, a fourth tubing segment connecting the second port of the first internal chamber to the second tubing segment, a fifth tubing segment connecting the first port of the second internal chamber to the first tubing segment, and a sixth tubing segment connecting the second port of the second internal chamber to the second tubing segment.

3. A system for performing a plasmapheresis procedure comprising a durable hardware component and the disposable fluid flow set of claim 2, the durable hardware component comprising a first tube clamp for controlling flow through the third and fifth tubing segments, a second tube clamp for controlling flow through the fourth and sixth tubing segments, and a programmable controller programmed to automatically actuate the first and second tube clamps to selectively permit or preclude flow through the third, fourth, fifth and sixth tubing segments in connection with performing a priming, collection or reinfusion phase of a plasmapheresis procedure.

4. The system of claim 3 wherein the programmable controller is further programmed i) to operate the system in a priming phase to pump anticoagulant solution through the disposable fluid flow set, to actuate the first tube clamp to permit anticoagulant to flow through the third tubing segment into the first internal chamber and to block flowthrough the fifth tubing segment into the second internal chamber and the second tube clamp to permit flow through the fourth tubing segment and block flow through the sixth tubing segment, ii) to operate the system in a collection phase to pump anticoagulant at a controlled rate to mix with whole blood, to actuate the first tube clamp to block flow through the third tubing segment and to permit flow of concentrated red blood cells through the fifth tubing segment into the second internal chamber and the second tube clamp to preclude flow through both the fourth tubing segment and the sixth tubing segment, iii) to operate the system in a reinfusion phase to pump concentrated red blood cells from the second internal chamber, to actuate the first tube clamp to preclude flow through the third tubing segment and fifth tubing segment and the second tube clamp permit flow out of the second internal chamber through the sixth tubing segment and prevent flow out of the first internal chamber through the fourth tubing segment, and iv) to actuate the second tube clamp to occlude both the fourth tubing segment and the sixth tubing segment.

5. A system for performing a plasmapheresis procedure comprising a durable hardware component and the disposable fluid flow set of claim 1, the durable hardware component comprising a first tube clamp for controlling flow through a third and fifth tubing segments, a second tube clamp for controlling flow through a fourth and sixth tubing segments, and a programmable controller programmed to automatically actuate the first and second tube clamps to selectively permit or preclude flow through the third, fourth, fifth and sixth tubing segments in connection with performing a priming, collection or reinfusion phase of a plasmapheresis procedure.

6. The system of claim 5 wherein the programmable controller is further programmed i) to operate the system in a priming phase to pump anticoagulant solution through the disposable fluid flow set, to actuate the first tube clamp to permit anticoagulant to flow through the third tubing segment into the first internal chamber and to block flowthrough the fifth tubing segment into the second internal chamber and the second tube clamp to permit flow through the fourth tubing segment and block flow through the sixth tubing segment, ii) to operate the system in a collection phase to pump anticoagulant at a controlled rate to mix with whole blood, to actuate the first tube clamp to block flow through the third tubing segment and to permit flow of concentrated red blood cells through the fifth tubing segment into the second internal chamber and the second tube clamp to preclude flow through both the fourth tubing segment and the sixth tubing segment, iii) to operate the system in a reinfusion phase to pump concentrated red blood cells from the second internal chamber, to actuate the first tube clamp to preclude flow through the third tubing segment and fifth tubing segment and the second tube clamp permit flow out of the second internal chamber through the sixth tubing segment and prevent flow out of the first internal chamber through the fourth tubing segment, and iv) to actuate the second tube clamp to occlude both the fourth tubing segment and the sixth tubing segment.

\* \* \* \* \*